United States Patent [19]

Caprathe et al.

[11] Patent Number: 4,988,699

[45] Date of Patent: Jan. 29, 1991

[54] SUBSTITUTED TETRAHYDROBENZOTHIAZOLES AS DOPAMINERGIC AGENTS

[75] Inventors: Bradley W. Caprathe, Redford; Juan C. Jaen, Plymouth; Lawrence D. Wise, Ann Arbor, all of Mich.

[73] Assignee: Warner-Lambert Company, Morris Plains, N.J.

[21] Appl. No.: 323,519

[22] Filed: Mar. 14, 1989

[51] Int. Cl.$^5$ .................... A61K 31/495; C07D 417/14
[52] U.S. Cl. ..................................... 514/254; 514/253; 544/360; 544/364
[58] Field of Search ................ 544/360, 364; 514/254, 514/253

[56] References Cited

U.S. PATENT DOCUMENTS

| | | | |
|---|---|---|---|
| 3,944,551 | 3/1976 | Regnier | 544/360 |
| 4,260,610 | 4/1981 | Regnier | 544/360 |
| 4,308,266 | 12/1981 | Seiler | 544/360 |
| 4,613,601 | 9/1986 | Regnier | 544/360 |
| 4,731,374 | 3/1988 | Griss | 514/367 |

FOREIGN PATENT DOCUMENTS 0177392  4/1986  European Pat. Off. .

*Primary Examiner*—Robert A. Wax
*Assistant Examiner*—Frederick F. Tsung
*Attorney, Agent, or Firm*—Francis J. Tinney

[57] ABSTRACT

Substituted tetrahydrobenzothiazoles are described, as well as methods for the preparation and pharmaceutical composition of same, which are useful as dopamine agonists with selectivity for the presynaptic dopamine receptor and are useful as dopaminergic, antipsychotic, and antihypertensive agents as well as for treating hyperprolactinaemia-related conditions and central nervous system disorders.

6 Claims, No Drawings

SUBSTITUTED TETRAHYDROBENZOTHIAZOLES AS DOPAMINERGIC AGENTS

BACKGROUND OF THE INVENTION

The present invention relates to novel substituted tetrahydrobenzothiazoles useful as pharmaceutical agents, to methods for their production, to pharmaceutical compositions which include these compounds and a pharmaceutically acceptable carrier, and to pharmaceutical methods of treatment. More particularly, the novel compounds of the present invention are dopamine agonists having selectivity for the presynaptic dopamine receptor, i.e., an autoreceptor. The advantage of an autoreceptor agonist is that it modulates the activity of dopaminergic systems selectively, without the postsynaptic stimulation which is inherent to nonselective dopamine agonists.

Compounds of Formula A

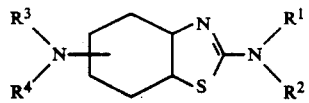

wherein $R^1$ represents a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, whilst the above-mentioned phenyl nuclei may be substituted by 1 or 2 halogen atoms, $R^2$ represents a hydrogen atom or an alkyl group with 1 to 4 carbon atoms, $R^3$ represents a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms, $R^4$ represents a hydrogen atom, an alkyl group with 1 to 4 carbon atoms, an alkenyl or alkynyl group having 3 to 6 carbon atoms or $R^3$ and $R^4$ together with the nitrogen atom between them represent a pyrrolidino, piperidino, hexamethyleneimino or morpholino group are disclosed in U.S. Pat. No. 4,731,374 as having pharmacological properties, particularly a hypotensive effect on blood pressure, a heart rate lowering effect, and an effect on the central nervous system, particularly a stimulant effect on the dopamine receptors.

However, the benzothiazoles disclosed in U.S. Pat. No. 4,731,374 do not suggest the combination of structural variations of the compounds of the present invention described hereinafter. Furthermore, the aforementioned thiazole derivatives are not disclosed as dopamine agonists having selectivity for the presynaptic dopamine receptor.

SUMMARY OF THE INVENTION

Accordingly, the present invention is a compound of Formula I

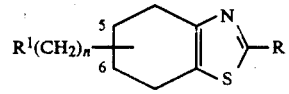

wherein R is hydrogen, lower alkyl or

wherein $R^4$ is hydrogen, lower alkyl, aryl lower alkyl, lower alkanoyl, aryl lower alkanoyl or aroyl and $R^3$ is hydrogen, lower alkyl or aryl lower alkyl; n is zero or an integer from 1 to 3; $R^1$ is

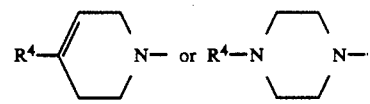

wherein $R^4$ is phenyl, phenyl substituted by lower alkyl, lower alkoxy, lower thioalkoxy, halogen, or trifluoromethyl, 2-, 3-, or 4-pyridinyl or 2-, 3-, or 4-pyridinyl substituted by lower alkyl, lower alkoxy or halogen, 2-, 4-, or 5-pyrimidinyl or 2-, 4-, or 5-pyrimidinyl substituted by lower alkyl, lower alkoxy or halogen, 2- or 3-thienyl or 2- or 3-thienyl substituted by lower alkyl or halogen and either

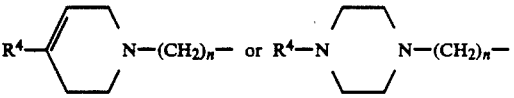

is attached at the 5 or 6 position of the tetrahydrobenzothiazole ring; and corresponding optical isomers thereof; or a pharmaceutically acceptable acid addition salt thereof.

As dopamine agonists with selectivity for the presynaptic dopamine receptor, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl lower alkyl" means an aromatic radical attached to a lower alkyl radical wherein lower alkyl is as defined above. The aromatic radical is a phenyl group or phenyl group substituted by one to four substituents selected from lower alkyl, lower alkoxy, lower thioalkoxy, halogen or trifluoromethyl such as, for example, benzyl, phenethyl, and the like.

The term "lower alkanoyl" means a lower alkyl group as defined above attached to a carbonyl group which is then attached to the parent molecular residue.

The term "aryl lower alkanoyl" means an aromatic radical, as defined above, attached to a lower alkanoyl group as defined above.

The term "aroyl" means an aromatic radical as defined above attached to a carbonyl group which is then attached to the parent molecular residue.

"Lower alkoxy" and "thioalkoxy" are O-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is hydrogen, or

wherein $R^2$ is hydrogen, lower alkyl, lower alkanoyl or aroyl, and $R^3$ is hydrogen, or lower alkyl and $R^1$ is

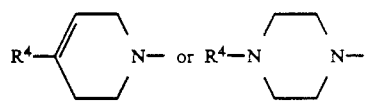

wherein $R^4$ is phenyl, 2-pyridinyl, 2-pyrimidinyl, or 2-thienyl.

Another preferred embodiment is a compound of Formula I wherein R is hydrogen or

wherein $R^2$ is hydrogen, lower alkanoyl, or aroyl, and $R^3$ is hydrogen and $R^1$ is

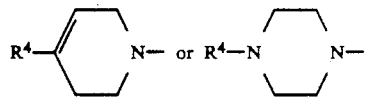

wherein $R^4$ is phenyl, 2-pyridinyl, 2-pyrimidinyl, or 2-thienyl.

Particularly valuable are:
(±)-4,5,6,7-Tetrahydro-6-[4-(2-pyridinyl)-1-piperazinyl]-2-benzothiazolamine;
(±)-6-(3,6-Dihydro-4-phenyl-1(2H)-pyridinyl)-4,5,6,7-tetrahydro-2-benzothiazolamine;
(±)-4,5,6,7-Tetrahydro-6-(4-phenyl-1-piperazinyl)-2-benzothiazolamine;
(±)-4,5,6,7-Tetrahydro-6-[4-(2-pyrimidinyl)-1-piperazinyl]-2-benzothiazolamine;
(±)-4,5,6,7-Tetrahydro-6-[4-(2-thienyl)-1-piperazinyl]-2-benzothiazolamine;
(±)-6-[3,6-Dihydro-4-(2-thienyl)-1(2H)-pyridinyl]-4,5,6,7-tetrahydro-2-benzothiazolamine;
(±)-4,5,6,7-Tetrahydro-6-[4-(2-pyridinyl)-1-piperazinyl]methyl]-2-benzothiazolamine;
(±)-6-[(3,6-Dihydro-4-phenyl-1(2H)-pyridinyl)-methyl]-4,5,6,7-tetrahydro-2-benzothiazolamine;
(±)-4,5,6,7-Tetrahydro-6-[(4-phenyl-1-piperazinyl)-methyl]-2-benzothiazolamine;
(±)-4,5,6,7-Tetrahydro-6-[4-(2-pyrimidinyl)-1-piperazinyl]methyl]-2-benzothiazolamine;
(±)-4,5,6,7-Tetrahydro-6-[[4-(2-thienyl)-1-piperazinyl]-methyl]-2-benzothiazolamine;
(±)-6-[[3,6-Dihydro-4-(2-thienyl)-1(2H)-pyridinyl]-methyl]-4,5,6,7-tetrahydro-2-benzothiazolamine;
(±)-4,5,6,7-Tetrahydro-6-[4-(2-pyridinyl)-1-piperazinyl]methyl]benzothiazole;

(±)-4,5,6,7-Tetrahydro-6-[2-[4-(2-pyridinyl)-1-piperazinyl]ethyl]-2-benzothiazolamine;
(±)-6-2-(3,6-Dihydro-4-phenyl-1(2H)-pyridinyl)-ethyl]-4,5,6,7-tetrahydro-2-benzothiazolamine;
(±)-4,5,6,7-Tetrahydro-6-[2-(4-phenyl-1-piperazinyl)ethyl]-2-benzothiazolamine;
(±)-4,5,6,7-Tetrahydro-6-[2-4-(2-pyrimidinyl)-1-piperazinyl]ethyl]-2-benzothiazolamine;
(±)-4,5,6,7-Tetrahydro-6-2-4-(2-thienyl)-1-piperazinyl]ethyl]-2-benzothiazolamine;
(±)-6-[2-[3,6-Dihydro-4-(2-thienyl)-1(2H)-pyridinyl]ethyl]-4,5,6,7-tetrahydro-2-benzothiazolamine;
(±)-4,5,6,7-Tetrahydro-5-[4-(2-pyridinyl)-1-piperazinyl]-2-benzothiazolamine;
(±)-4,5,6,7-Tetrahydro-5-[4-(2-pyridinyl)-1-piperazinyl]methyl]-2-benzothiazolamine;
(±)-4,5,6,7-Tetrahydro-5-2-[4-(2-pyridinyl)-1-piperazinyl]ethyl]-2-benzothiazolamine;
(±)-5-[(3,6-Dihydro-4-phenyl-1(2H)-pyridinyl)methyl]4,5,6,7-tetrahydro-2-benzothiazolamine;
(±)-N-4,5,6,7-Tetrahydro-6-[4-(2-pyridinyl)-1-piperazinyl]-2-benzothiazolyl]benzamide;
(±)-N-4,5,6,7-Tetrahydro-6-[4-(2-pyridinyl)-1-piperazinyl]-2-benzothiazolyl]acetamide;
(±)-N-[4,5,6,7-Tetrahydro-6-[4-(2-pyridinyl)-1-piperazinyl]-2-benzothiazolyl]-2-methylpropanamide;
(+)-4,5,6,7-Tetrahydro-6-[4-(2-pyridinyl)-1-piperazinyl]-2-benzothiazolamine;
(−)-4,5,6,7-Tetrahydro-6-[4-(2-pyridinyl)-1-piperazinyl]-2-benzothiazolamine;
(+)-4,5,6,7-Tetrahydro-6-[2-[4-(2-pyridinyl)-1-piperazinyl]ethyl]-2-benzothiazolamine; and
(−)-4,5,6,7-Tetrahydro-6-2-4-(2-pyridinyl)-1-piperazinyl]ethyl]-2-benzothiazolamine; or a pharmaceutically acceptable acid addition salt thereof.

The compounds of Formula I are valuable dopaminergic agents. The tests employed indicate that compounds of Formula I possess dopamine agonist activity with selectivity for the presynaptic dopamine receptor (autoreceptor). Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit haloperidol binding in a receptor assay described by D. R. Burt, et al, *Molecular Pharmacology*, Volume 12, pages 800–812 (1976); and for their ability to inhibit dopamine synthesis in rats according to the protocol described by J. R. Walters and R. H. Roth, *Naunyn—Schmiedeberg's Archives of Pharmacology*, Volume 296, pages 5–14 (1976). The above test methods are incorporated herein by reference. The data in the table shows the selective presynaptic dopamine agonist activity of representative compounds of Formula I.

| | Biological Activity of Compounds of Formula I | | | |
|---|---|---|---|---|
| Example Number | Compound | Inhibition of Haloperidol Binding IC$_{50}$ nM | Inhibition of Locomotor Activity in Mice ED$_{50}$, mg/kg, IP | Inhibition of Dopamine Synthesis in Rats |
| 1 | (±)-4,5,6,7-Tetrahydro-6-[4-(2-pyridinyl)-1-piperazinyl]-2-benzothiazolamine | 876 | 6.6 | 50% at 4.4 mg/kg, IP |
| 3 | (+)-4,5,6,7-Tetrahydro-6-[4-(2-pyridinyl)-1-piperazinyl]-2-benzothiazolamine | ~800 | 9.9 | 50% at 7.0 mg/kg, IP |
| 4 | (−)-4,5,6,7-Tetrahydro-6-[4-(2-pyridinyl)-1-piperazinyl]-2-benzothiazolamine | ~1500 | 7.4 | 50% at 4.8 mg/kg, IP |
| 1c | (±)-4,5,6,7-Tetrahydro-6-[4-(2-pyrimidinyl)-1-piperazinyl]-2-benzothiazolamine | | 30 | |
| 5 | (±)-4,5,6,7-Tetrahydro-6-[[4-(2-pyridinyl)-1-piperazinyl]methyl]-benzothiazole | | 7.4 | |
| 2 | (±)-N-[4,5,6,7-Tetrahydro-6-[4-(2-pyridinyl)-1-piperazinyl]-2-benzothiazolyl]benzamide | | 3.7 | 59% at 10 mg/kg, IP |
| 9 | (±)-4,5,6,7-Tetrahydro-6-[2-[4-(2-pyridinyl)-1-piperazinyl]ethyl]-2-benzothiazolamine | 105 | 0.21 | 50% at 1.3 mg/kg, IP |
| 11a | (−)-4,5,6,7-Tetrahydro-6-[2-[4-(2-pyridinyl)-1-piperazinyl]ethyl]-2-benzothiazolamine | | 0.20 | 50% at 0.2 mg/kg, IP |
| 11 | (+)-4,5,6,7-Tetrahydro-6-[2-[4-(2-pyridinyl)-1-piperazinyl]ethyl]-2-benzothiazolamine | | 0.37 | 50% at 0.8 mg/kg, IP |
| 7 | (±)-4,5,6,7-Tetrahydro-6-[[4-(2-pyridinyl)-1-piperazinyl]methyl]-2-benzothiazolamine | | 7.2 | 48% at 10 mg/kg, IP |
| 8 | (±)-6-[(3,6-Dihydro-4-phenyl-1(2H)-pyridinyl)methyl]-4,5,6,7-tetrahydro-2-benzothiazolamine | | 0.75 | |
| 1a | (±)-6-(3,6-Dihydro-4-phenyl-1(2H)-pyridinyl)-4,5,6,7-tetrahydro-2-benzothiazolamine | | 1.5 | 69% at 10 mg/kg, IP |
| 1b | (±)-4,5,6,7-Tetrahydro-6-(4-phenyl-1-piperazinyl)-2-benzothiazolamine | | 6.1 | |
| 10 | (±)-6-[2-(3,6-Dihydro-4-phenyl-1(2H)-pyridinyl)ethyl]-4,5,6,7-tetrahydro- | | 0.40 | |

-continued

Biological Activity of Compounds of Formula I

| Example Number | Compound | Inhibition of Haloperidol Binding IC$_{50}$ nM | Inhibition of Locomotor Activity in Mice ED$_{50}$, mg/kg, IP | Inhibition of Dopamine Synthesis in Rats |
|---|---|---|---|---|
| | 2-benzothiazolamine | — | | |

A compound of the Formula I

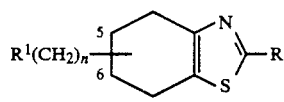

wherein R is hydrogen, lower alkyl or

wherein $R^2$ is hydrogen, lower alkyl, aryl lower alkyl, lower alkanoyl, aryl lower alkanoyl or aroyl and $R^3$ is hydrogen, lower alkyl or aryl lower alkyl; n is zero or an integer from 1 to 3; $R^1$ is

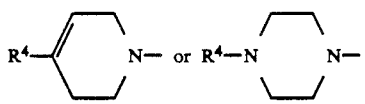

wherein $R^4$ is phenyl, phenyl substituted by lower alkyl, lower alkoxy, lower thioalkoxy, halogen, or trifluoromethyl, 2-, 3-, or 4-pyridinyl or 2-, 3-, or 4-pyridinyl substituted by lower alkyl, lower alkoxy or halogen, 2-, 4-, or 5-pyrimidinyl or 2-, 4-, or 5-pyrimidinyl substituted by lower alkyl, lower alkoxy or halogen, 2- or 3-thienyl or 2- or 3-thienyl substituted by lower alkyl or halogen and either

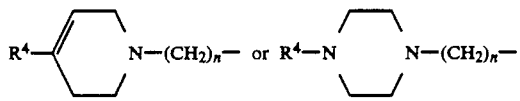

is attached at the 5 or 6 position of the tetrahydrobenzothiazole ring; and corresponding optical isomers thereof; or a pharmaceutically acceptable acid addition salt thereof, may be prepared by reacting a compound of Formula II

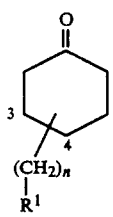

wherein $R^1$ and n are as defined above with a compound of Formula III

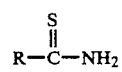

wherein R is as defined above in the presence of an oxidizing agent such as a halogen, sulfuryl chloride, thionyl chloride, chlorosulfonic acid, sulfur monochloride, and the like using the methodology described by Dodson, R. M. and King, L. C., *Journal of American Chemical Society*, Volume 67, pages 2242–2243 (1945) and Volume 68, page 871 (1946) or formamidine disulfide dihydrochloride using the methodology described by King, L. C. and Ryden, I., *Journal of American Chemical Society*, Volume 69, pages 1813–1814 (1947) to give a compound of Formula I.

Alternatively, a compound of Formula I is prepared by treating a compound of Formula II with a halogen such as, for example, chlorine or bromine in a protic solvent such as, for example, methanol, glacial acetic acid, hydrogen bromide in acetic acid, and the like. The solvent is removed and the resulting bromo ketone is reacted with a compound of Formula III in the presence of a solvent such as, for example, ethanol and the like to give a compound of Formula I.

Additionally, a compound of Formula I is prepared by treating a compound of Formula IV

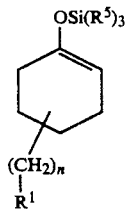

wherein $R^5$ is lower alkyl and $R^1$ and n are as defined above, with a halogenating agent such as, for example, bromine, chlorine, N-chlorosuccinimide, N-bromosuccinimide, and the like. Subsequent addition to the previous mixture of a compound of Formula III in the presence of an inert solvent such as, for example, tetrahydrofuran and the like gives a compound of Formula I.

A compound of Formula IV is prepared by adding a solution of a compound of Formula II in an inert solvent such as, for example, tetrahydrofuran and the like at about −78° C. to a solution of lithium diisopropylamide in an inert solvent such as, for example, tetrahydrofuran and the like over about a 20-minute period. Subsequent addition to the previous mixture of a compound of the Formula $(R^5)_3$SiCl wherein $R^5$ is as defined above gives a compound of Formula IV.

A compound of Formula II is prepared from a compound of Formula V

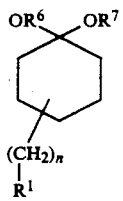

wherein $R^6$ and $R^7$ are alkyl of one to six carbon atoms or $R^6$ and $R^7$ together are

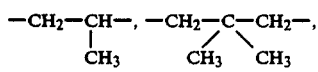

—$CH_2CH_2$— or —$CH_2CH_2CH_2$— and $R^1$ and n are as defined above by treatment with an acid such as, for example, a 10% aqueous solution of hydrochloric acid in the presence of an inert solvent such as, for example, acetone and the like to give a compound of Formula II.

A compound of Formula Va

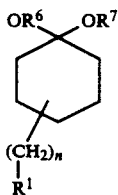

wherein n is zero and $R^1$, $R^6$, and $R^7$ are as defined above is prepared from a compound of Formula VI

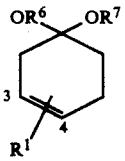

wherein $R^1$, $R^6$, and $R^7$, are as defined above by treatment with a reducing agent such as, for example, sodium cyanoborohydride and the like in a solvent such as, for example, methanol and the like in the presence of an acid such as, for example, hydrochloric acid and the like or alternatively reduction is carried out with hydrogen in the presence of a catalyst such as, for example, palladium on carbon in the presence of a solvent such as, for example, methanol and the like to give a compound of Formula Va.

A compound of Formula VI is prepared from a compound of Formula VII

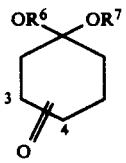

wherein $R^6$ and $R^7$ are as defined above by reaction with a compound of Formula VIII $R^1H$      VIII wherein $R^1$ is as defined above in the presence of a catalytic amount of an acid such as, for example, para-toluenesulfonic acid and the like in the presence of an inert solvent suited for the azeotropic removal of water such as, for example, toluene and the like to give a compound of Formula VI.

A compound of Formula IIa,

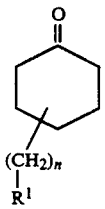

wherein n is zero, $R^1$ is as defined above, and $R^1(CH_2)_n$— is attached to the 3 position of the cyclohexane ring is prepared by reaction of cyclohexen-2-one with a compound of Formula VIII, wherein $R^1$ is as defined above in the presence of a small amount of a polar solvent such as water.

A compound of Formula V wherein n is an integer from 1 to 3 and $R^1$, $R^6$, and $R^7$ are as defined above is prepared from a compound of Formula IX

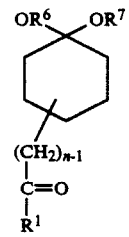

wherein n is an integer from 1 to 3 and $R^1$, $R^6$, and $R^7$ are as defined above by treatment with a reducing agent such as, for example, diborane, aluminum hydride and the like in an inert solvent such as, for example, tetrahydrofuran and the like to give a compound of Formula V.

A compound of Formula IX is prepared from a compound of Formula X

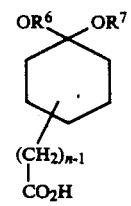

wherein n is an integer from 1 to 3 and $R^6$ and $R^7$ are as defined above and a compound of Formula VIII. In order to obtain the reaction of these two compounds, a compound of Formula X must be activated in the presence of a chloroformate such as, for example, isobutyl chloroformate and a base such as, for example, triethylamine, or alternately, a coupling reagent such as, for example, dicyclohexylcarbodiimide, carbonyldiimidazole and the like in the presence of an inert solvent such as, for example, dichloromethane and the like to give a compound of Formula IX.

A compound of Formula X is prepared from a compound of Formula XI

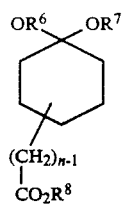

wherein n is an integer from 1 to 3, $R^8$ is lower alkyl and $R^6$ and $R^7$ are as defined above, by hydrolysis with a base such as, for example, potassium hydroxide and the like in an alcohol such as, for example, ethanol and the like to give a compound of Formula X.

A compound of Formula XI is prepared from a compound of Formula XII

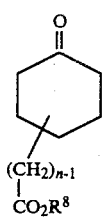

wherein n is an integer from 1 to 3 and $R^8$ is as defined above using conventional procedures known in the art.

Alternatively, a compound of Formula V is prepared from a compound of Formula XIII

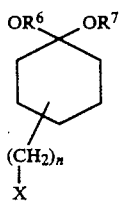

wherein n is an integer from 1 to 3, X is halogen, $CH_3$—$SO_2O$—, para—$CH_3C_6H_4SO_2O$—, and the like, and $R^6$, and $R^7$ are as defined above and a compound of Formula VIII in the presence of a base such as, for example, sodium bicarbonate and the like and a solvent such as, for example, dimethylformamide and the like to give a compound of Formula V.

A compound of Formula XIII is prepared from a compound of Formula XIV

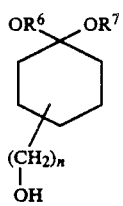

wherein n is an integer from 1 to 3 and $R^6$ and $R^7$ are as defined above by treatment with thionyl chloride, thionyl bromide and the like in the presence of an inert solvent such as, for example, chloroform and the like or alternatively treatment with methanesulfonyl chloride, para-toluenesulfonyl chloride and the like in the presence of a base such as, for example, pyridine and the like to give a compound of Formula XIII.

A compound of Formula XIV is prepared from a compound of Formula XI wherein n is an integer from 1 to 3 and $R^6$, $R^7$, and $R^8$ are as defined above by treatment with a complex metal hydride such as, for example, diborane, lithium aluminum hydride and the like in the presence of a solvent such as, for example, tetrahydrofuran and the like to give a compound of Formula XIV.

Alternatively, a compound of Formula I

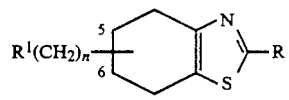

wherein n is an integer from 1 to 3 and R and $R^1$ are as defined above is prepared from a compound of Formula XV

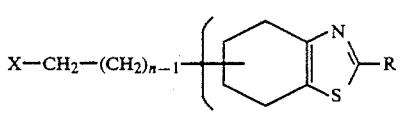

wherein n is an integer from 1 to 3 and X and R are as defined above, and a compound of Formula VIII using the methodology previously described for preparing a compound of Formula V from a compound of Formula XIII.

A compound of Formula XV is prepared from a compound of Formula XVI

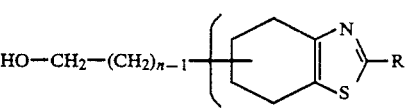

wherein n is an integer from 1 to 3 and R is as defined above, using the methodology previously described for preparing a compound of Formula XIII from a compound of Formula XIV.

A compound of Formula XVI is prepared from a compound of Formula XVI

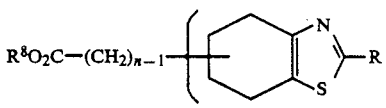

wherein n is an integer from 1 to 3 and R and $R^8$ are as defined above by treatment with a complex metal hydride such as, for example, diborane, lithium aluminum hydride and the like in the presence of a solvent such as, for example, tetrahydrofuran and the like to give a compound of Formula XVI.

A compound of Formula XVII is prepared from a compound of Formula XII wherein n is an integer from 1 to 3 and $R^8$ is as defined above by using the methodology previously described for preparing a compound of Formula I from a compound of Formula II and a compound of Formula III.

Alternatively, a compound of Formula I wherein n is an integer from 1 to 3 and R and R¹ are as defined above is prepared from a compound of Formula XVIII

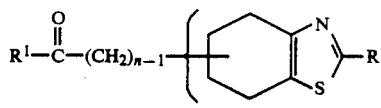   XVIII wherein n is an integer from 1 to 3 and R and R¹ are as defined above by using the methodology previously described for preparing a compound of Formula V from a compound of Formula IX.

A compound of Formula XVIII is prepared from a compound of Formula XIX

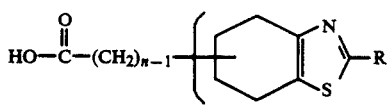   XIX wherein n is an integer from 1 to 3 and R is as defined above by using the methodology previously described for preparing a compound of Formula IX from a compound of Formula X.

A compound of Formula XIX is prepared from a compound of Formula XVII wherein n is an integer from 1 to 3 and R and R⁸ are as defined above by using the methodology previously described for preparing a compound of Formula X from a compound of Formula XI.

Preferably a compound of Formula Ib

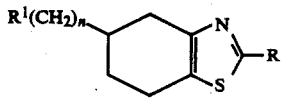   Ib wherein n is zero and R and R¹ are as defined above is prepared from a compound of Formula XX

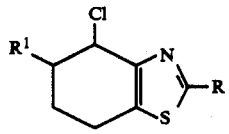   XX wherein R and R¹ are as defined above by treatment with zinc in the presence of an acid such as, for example, glacial acetic acid and the like to give a compound of Formula Ib.

A compound of Formula XX is prepared from a compound of Formula XXI,

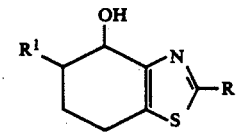   XXI wherein R and R¹ are as defined above by treatment with a halogenating agent such as, for example, thionyl chloride and the like in the presence of a solvent such as, for example, chloroform and the like to give a compound of Formula XX.

A compound of Formula XXI is prepared from a compound of Formula XXII

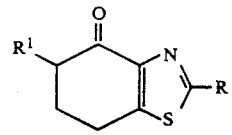   XXII wherein R and R¹ are as defined above by reduction with a complex metal hydride such as, for example, sodium borohydride and the like in an inert solvent such as methanol and the like to give a compound of Formula XXI.

A compound of Formula XXII is prepared from a compound of Formula XXIII

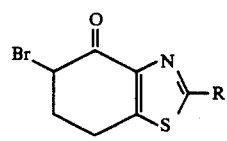   XXIII wherein R is as defined above and a compound of Formula VIII in the presence of a base such as, for example, triethylamine and the like or sodium bicarbonate and the like in an inert solvent such as, for example, chloroform and the like to give a compound of Formula XXII.

A compound of Formula XXIII is prepared from a compound of Formula XXIV

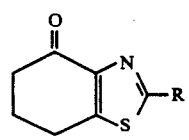   XXIV wherein R is as defined above by treatment with bromine in hydrobromic acid to give a compound of Formula XXIII.

A compound of Formula XXIV is prepared from the compound of Formula XXV

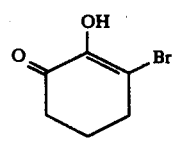   XXV and a compound of Formula III using the methodology previously described for preparing a compound of Formula I from a compound of Formula II and a compound of Formula III.

The compound of Formula XXV is prepared from the compound of Formula XXVI

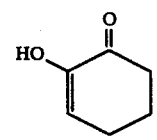   XXVI and N-bromosuccinimide in the presence of an inert solvent such as, for example, tetrahydrofuran and the like to give the compound of Formula XXV.

Compounds of Formula VII and Formula XII are either known or capable of being prepared by methods known in the art.

A compound of Formula I, which is a racemic mixture, may be further resolved into its enantiomers. Accordingly, as another aspect of the present invention, a compound of Formula ($\pm$)I may be resolved into its enantiomers by the use of optically active acids. Thus, for example, when R is $NH_2$ and n is zero, a compound of Formula ($\pm$)I is first converted to an amide derivative such as, for example, the isobutyramide derivative. The isobutyramide derivative is reacted with an optically active acid, such as, for example, (+)-di-para-toluoyl-D-tartaric acid or (−)-di-para-toluoyl-L-tartaric acid, and the like. Separation of the resulting diastereomeric salts by crystallization followed by neutralization and hydrolysis of the amide group affords the optically active enantiomer (+)I or (−)I.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

($\pm$)-4,5,6,7-Tetrahydro-6-[4-(2-pyridinyl)-1-piperazinyl]-2-benzothiazolamine

Method A

A solution of dry diisopropylamine (18.69 g) in 750 ml of anhydrous tetrahydrofuran is placed under a nitrogen atmosphere and cooled to 0° C. To this solution is added n-butyllithium (106 ml of a 1.6 M hexane solution) dropwise. The mixture is cooled to −78° C. and a solution of 4-[4-(2-pyridinyl)-1-piperazinyl]cyclohexanone (33.0 g) (Example A) in 250 ml of tetrahydrofuran is added dropwise over a 20-minute period. The mixture is stirred at −78° C. for an additional 20 minutes and then quenched with trimethylsilyl chloride (20.10 g). The reaction mixture is allowed to gradually warm to room temperature and the solvent is evaporated in vacuo. The residue is taken up into 500 ml of diethyl ether, filtered through Celite, and purified by flash chromatography (silica gel; ethyl acetate) to yield 36.5 g of 1-(2-pyridinyl)-4-[[4-(trimethylsilyl)oxy]-3-cyclohexen-1-yl]piperazine as a colorless oil. This compound is dissolved in 750 ml of anhydrous tetrahydrofuran. The solution is cooled to 0° C. and N-bromosuccinimide (21.53 g; recrystallized from water, and dried in a vacuum oven) is added in small portions. The mixture is stirred at 0° C. for 10 minutes, thiourea (9.20 g) is added, and the mixture is refluxed for one hour. A colorless salt forms in the reaction flask which is filtered and dried to yield 46.0 g of the title compound as its monohydrobromide monohydrate salt; mp 199°–202° C.

Method B

4-[4-(2-Pyridinyl)-1-piperazinyl]cyclohexanone (15.37 g) (Example A) is intimately mixed with thiourea (9.12 g) by grinding them together in a mortar. To this mixture is added iodine (15.23 g) and the resulting paste is heated at 175° C. under a flow of nitrogen for about three hours, during which time the mixture is stirred frequently with a glass rod. The mixture is taken up into boiling water (500 ml) and the insoluble material is gravity-filtered. The cooled filtrate is made basic with ammonium hydroxide. The product is extracted into dichloromethane and purified by medium-pressure liquid chromatography (MPLC) to give the title compound as its hemihydrate; mp 223°–226° C.

Method C

4-[4-(2-Pyridinyl)-1-piperazinyl]cyclohexanone (8.3 g) (Example A) is dissolved in 85 ml of glacial acetic acid and 9 ml of 30% hydrobromic acid in acetic acid. Bromine (5.62 g) is added dropwise to this solution. A precipitate forms which is dissolved by addition of 40 ml of water. The resulting dark solution is stirred at room temperature overnight. The solvent is evaporated in vacuo and the residue is dissolved in 100 ml of ethanol and 25 ml of water. Thiourea (2.68 g) is added and the mixture is refluxed for about four hours. The solvent is then removed in vacuo and the residue is partitioned between ethyl acetate and dilute ammonium hydroxide solution. The organic phase is dried and evaporated. The crude product is purified by MPLC to yield the hemihydrate of the title compound as a beige solid; mp 223°–226° C. Also from this reaction mixture is isolated 6-[4-(5-bromo-2-pyridinyl)-1-piperazinyl]-4,5,6,7-tetrahydro-2-benzothiazolamine; mp 246°–248° C., as a by-product.

In a process analogous to Example 1 (Method B) using appropriate starting materials the corresponding compounds of Formula I are prepared as follows:

EXAMPLE 1a (±)-6-(3,6-Dihydro-4-phenyl-1(2H)-pyridinyl)-4,5,6,7-tetrahydro-2-benzothiazolamine mp 222°–226° C. (free base), mp 297°–304° C. (dihydrochloride salt).

EXAMPLE 1b (±)-4,5,6,7-Tetrahydro-6-(4-phenyl-1-piperazinyl)-2-benzothiazolamine (¼ hydrate)

mp 244°–247° C.

EXAMPLE 1c (±)-4,5,6,7-Tetrahydro-6-4-(2-pyrimidinyl)-1-piperazinyl-2-benzothiazolamine (hemihydrate)

mp 204°–207° C.

EXAMPLE 2

(±)-N-[4,5,6,7-Tetrahydro-6-[4-(2-pyridinyl)-1-piperazinyl]-2-benzothiazolyl]benzamide A solution of (±)-4,5,6,7-tetrahydro-6-[4-(2-pyridinyl)-1-piperazinyl]-2-benzothiazolamine (10.0 g) (Example 1) in 200 ml of chloroform is treated with triethylamine (6.06 g) and benzoyl chloride (4.21 g). The resulting red solution is refluxed for two hours under nitrogen. Saturated sodium bicarbonate solution is added. The organic layer is dried (magnesium sulfate) and evaporated. The residue is purified by MPLC (silica; 1.5% methanol, 98.5% dichloromethane). The title compound is obtained as a yellow solid; mp 230°–232° C.

In a process analogous to Example 2 using appropriate starting materials the corresponding compounds of Formula I are prepared as follows:

EXAMPLE 2a (±)-N-4,5,6,7-Tetrahydro-6-[4-(2-pyridinyl)-1-piperazinyl-2-benzothiazolyl]acetamide mp 239°–242° C.

EXAMPLE 2b (±)-N-4,5,6,7-Tetrahydro-6-[4-(2-pyridinyl)-1-piperazinyl]-2-benzothiazolyl]-2-methylpropanamide mp 158°–159.5° C.

EXAMPLE 3

(+)-4,5,6,7-Tetrahydro-6-[4-(2-pyridinyl)-1-piperazinyl]-2-benzothiazolamine

A solution of (±)-N-[4,5,6,7-tetrahydro-6-[4-(2-pyridinyl)-1-piperazinyl]-2-benzothiazolyl]-2-methylpropanamide (18.57 g) (Example 2b) in 150 ml of 95% ethanol is mixed with a solution of (+)-di-p-toluoyl-D-tartaric acid (19.48 g) in 100 ml of 95% ethanol. The mixture is evaporated in vacuo and the residue recrystallized from 95% ethanol three times. The resulting salt is partitioned between chloroform and a dilute solution of ammonium hydroxide. The organic phase is dried over magnesium sulfate and evaporated in vacuo to leave 5.84 g of a foamy white solid which is refluxed in 250 ml of a 10% solution of hydrochloric acid for 12 hours. The solution is cooled and titrated with a concentrated solution of ammonium hydroxide to pH 10. The compound is extracted into chloroform and dried over magnesium sulfate. The solvent is evaporated in vacuo to yield 2.86 g of (+)-4,5,6,7-tetrahydro-6-[4-(2-pyridinyl)-1-piperazinyl]-2-benzothiazolamine hemihydrate as a white solid; mp 227°–231° C.; $[\alpha]_D$ +64.3° (c=1.25 methanol).

EXAMPLE 4

(−)-4,5,6,7-Tetrahydro-6-[4-(2-pyridinyl)-1-piperazinyl]-2-benzothiazolamine.

In a process analogous to Example 3 by substituting (−)-di-p-toluoyl-L-tartaric acid for (+)-di-p-toluoyl-D-tartaric acid as the resolving agent one obtains (−)-4,5,6,7-Tetrahydro-6-[4-(2-pyridinyl)-1-piperazinyl]-2-benzothiazolamine, containing ½ molecule of $H_2O$; mp 230°-232° C.; $[\alpha]_D$ −61.4° (c=0.95, methanol).

EXAMPLE 5

(±)-4,5,6,7-Tetrahydro-6-[[4-(2-pyridinyl)-1piperazinyl]methyl]benzothiazole

A solution of (±)-ethyl 2-amino-4,5,6,7-tetrahydro-6-benzothiazolecarboxylate (13.5 g) (Example C) in 700 ml of anhydrous tetrahydrofuran is cooled in an ice bath and lithium aluminum hydride (4.56 g) is added in small portions. A thick suspension forms which is kept at room temperature for one hour. The reaction mixture is quenched by careful addition of a 10% solution of hydrochloric acid. The volatile components are evaporated in vacuo and the residue is stirred with a 25% solution of sodium hydroxide and dichloromethane for 30 minutes. An emulsion forms which is filtered through Celite. The aqueous phase is extracted with dichloromethane several times. The pooled organic extracts are dried and evaporated. The residue is recrystallized from ethyl acetate to give (±)-4,5,6,7-tetrahydro-6-benzothiazolemethanol as a colorless solid, mp 176°-182° C. A solution of this compound (5.0 g) in 500 ml of chloroform is treated with 25 ml of a 1 M hydrochloric acid-diethyl ether solution, followed by 50 ml of thionyl chloride. The reaction mixture is refluxed under nitrogen for one hour until evolution of gas ceases. The mixture is concentrated in vacuo and the residue is taken up into 100 ml of dimethylformamide. To this solution is added 1-(2-pyridyl)piperazine (4.89 g) and sodium bicarbonate (5.0 g) and the mixture is heated at 85° C. for six hours. The solvent is evaporated in vacuo, and the residue is partitioned between dichloromethane and water. The organic layer is dried (magnesium sulfate) and purified by MPLC. The hydrochloride salt is prepared to give (±)-4,5,6,7-tetrahydro-6-[[4-(2-pyridinyl)-1-piperazinyl]methyl]benzothiazole containing 2.85 molecules of hydrochloric acid and 1.1 molecules of water; mp 251°-252° C.

EXAMPLE 6

(±)-1-(2-Amino-4,5,6,7-tetrahydro-6-benzothiazolyl)-carbonyl]-4-(2-pyridinyl)piperazine.

A solution of (±)-2-amino-4,5,6,7-tetrahydro-6-benzothiazolecarboxylic acid (1.0 g) (Example E), 1-hydroxybenzotriazole hydrate (0.68 g), and 1-(2-pyridyl)piperazine (0.82 g) in 20 ml of dimethylformamide is cooled in an ice bath under nitrogen. Solid N,N'-dicyclohexylcarbodiimide (1.03 g) is added at once and the resulting solution is stirred at room temperature for six hours. The solid which forms is filtered through Celite and discarded; the filtrate is evaporated in vacuo and the residue is partitioned between ethyl acetate and saturated sodium bicarbonate. The organic extract is washed with brine and dried (magnesium sulfate). The solvent is evaporated and the residue is purified by MPLC (silica; 2% methanol, 98% ethyl acetate). The title compound is obtained as a colorless solid; mp 224°-226° C.

In a process analogous to Example 6 using appropriate starting materials the corresponding compounds of Formula I are prepared as follows:

EXAMPLE 6a (±)-1-[(2-Amino-4,5,6,7-tetrahydro-6-benzothiazolyl)-carbonyl]-1,2,3,6-tetrahydro-4-phenylpyridine mp 214°-217° C.

EXAMPLE 6b (±)-1-[(2-Amino-4,5,6,7-tetrahydro-6-benzothiazolyl)-carbonyl]-1,2,3,6-tetrahydro-4-(2-thienyl)pyridine mp 165°-170° C.

EXAMPLE 6c (±)-1-[(2-Amino-4,5,6,7-tetrahydro-6-benzothiazolyl)-carbonyl]-4-(2-pyrimidinyl]piperazine mp 200°-215° C.

EXAMPLE 7

(±)-4,5,6,7-Tetrahydro-6-[[4-(2-pyridinyl)-1-piperazinyl]methyl]-2-benzothiazolamine A solution of (±)-1-[(2-amino-4,5,6,7-tetrahydro-6-benzothiazolyl)carbonyl]-4-(2-pyridinyl)-piperazine (2.8 g) (Example 6) in 200 ml of anhydrous tetrahydrofuran is treated with sodium borohydride (1.0 g) under nitrogen. The mixture is cooled in an ice bath and treated with boron trifluoride etherate (3.93 ml) dropwise. The reaction mixture is stirred at room temperature overnight, and quenched with 5 ml of glacial acetic acid. The mixture is evaporated in vacuo and the residue dissolved in 200 ml of a 10% solution of hydrochloric acid and refluxed for about 30 minutes. The solution is cooled in an ice bath and made basic with a concentrated solution of ammonium hydroxide and extracted with chloroform. The organic extract is dried (magnesium sulfate) and evaporated. The residue is triturated with 50 ml of warm diethyl ether and, after cooling to room temperature, is filtered. The title compound is obtained as a colorless solid; mp 177°-179° C.

EXAMPLE 8

(±)-6-[(3,6-Dihydro-4-phenyl-1(2H)-pyridinyl)methyl]-4,5,6,7-tetrahydro-2-benzothiazolamine An ice-cold solution of aluminum chloride (0.80 g) in 20 ml of diethyl ether is added dropwise to a suspension of lithium aluminum chloride (0.65 g) in 30 ml of tetrahydrofuran and 30 ml of diethyl ether under nitrogen. The mixture is stirred at room temperature for 15 minutes and a solution of (±)-1-[(2-amino-4,5,6,7-tetrahydro-6-benzothiazolyl)-carbonyl]-1,2,3,6-tetrahydro-4-phenylpyridine (3.5 g) (Example 6a) in 50 ml of tetrahydrofuran is added dropwise. The reaction mixture is stirred at 40° C. for 30 minutes. After cooling in an ice bath, the reaction is quenched by careful addition of 4 ml of a 10% solution of hydrochloric acid, 4 ml of a 30% solution of sodium hydroxide and 4 ml of water. The salts that precipitate are filtered through Celite and the filtrate evaporated and purified by MPLC (silica; 5% methanol, 95% dichloromethane). The title compound is obtained as a beige solid; mp 187°-190° C.

In a process analogous to Example 8 using appropriate starting materials the corresponding compound of Formula I is prepared as follows:

EXAMPLE 8a (±)-6-[3,6-Dihydro-4-(2-thienyl)-1(2H)-pyridinyl]-methyl]-4,5,6,7-tetrahydro-2-benzothiazolamine mp 177°–180° C.

EXAMPLE 9

(±)-4,5,6,7-Tetrahydro-6-[2-[4-(2-pyridinyl)-1-piperazinyl]ethyl]-2-benzothiazolamine Thiourea (7.56 g) and iodine (12.61 g) are mixed and stirred mechanically under a stream of nitrogen. To this mixture is added 4-[2-[4-(2-pyridinyl)-1-piperazinyl]ethyl]cyclohexanone (9.52 g) (Example J) and the temperature gradually increased to 150° C. Following 30 minutes at this temperature, the mixture is cooled to room temperature and treated with 250 ml of a 10% solution of hydrochloric acid. Some insoluble material is filtered, the filtrate made basic with ammonium hydroxide, and extracted with chloroform (2×500 ml). The combined organic extracts are dried over magnesium sulfate and concentrated. The crude reaction mixture is purified by MPLC (silica; 5% methanol, 95% chloroform) to give the title compound as a light yellow solid; mp 194°–197° C.

EXAMPLE 10

(±)-6-[2-(3,6-dihydro-4-phenyl-1(2H)-pyridinyl)-ethyl]-4,5,6,7-tetrahydro-2-benzothiazolamine Using the procedure described in Example 1 (Method A) 4-[2-(3,6-dihydro-4-phenyl-1(2H)-pyridinyl)-ethyl]-cyclohexanone (Example K) is converted into the title compound; mp 177°–182° C.

EXAMPLE 11

(+)-4,5,6,7-Tetrahydro-6-[2-[4-(2-pyridinyl)-1-piperazinyl]ethyl]-2-benzothiazolamine To a solution of (+)-1-[(2-amino-4,5,6,7-tetrahydro-6-benzothiazolyl)acetyl]-4-(2-pyridyl)piperazine (2.70 g) (Example M) in 250 ml of tetrahydrofuran is added sodium borohydride (1.07 g) under nitrogen. This suspension is cooled in an ice bath and boron trifluoride etherate (4.6 ml) added dropwise. The mixture is stirred at room temperature for one hour and the solvent removed in vacuo. The residue is dissolved in 250 ml of a 10% solution of hydrochloric acid and stirred for two hours. The solution is made basic with ammonium hydroxide and extracted with chloroform (2×200 ml). The combined chloroform extracts are dried (magnesium sulfate), filtered, and concentrated. The residue is purified by MPLC (silica; 5% methanol, 95% chloroform) to give 1.74 g of (+)-4,5,6,7-tetrahydro-6-[2-[4-(2-pyridinyl)-1-piperazinyl]ethyl]-2-benzothiazolamine, containing one-fourth of a molecule of water, as a colorless solid; mp 176°–190° C.; $[\alpha]_D = +52.2°$ (c=1.02; 0.1 N hydrochloric acid solution).

In a process analogous to Example 11 using appropriate starting materials the corresponding compound of Formula I is prepared as follows:

EXAMPLE 11a (−)-4,5,6,7-Tetrahydro-6-[2-[4-[2-pyridinyl)-1-piperazinyl]ethyl]-2-benzothiazolamine mp 176°–186° C.; $[\alpha]_D = -48.4°$ (c=1.01; 0.1N hydrochloric acid solution).

Preparation of Starting Material

EXAMPLE A

4-[4-(2-Pyridinyl)-1-piperazinyl]-cyclohexanone

A solution of 1,4-cyclohexanedione monoethyleneketal (50.0 g), 1-(2-pyridyl)piperazine (52.16 g), and p-toluenesulfonic acid (0.5 g) in 500 ml of toluene is refluxed with a Dean-Stark trap until the theoretical amount of water is collected (about four hours). The solvent is evaporated in vacuo and the residue is dissolved in 750 ml of methanol. This solution is cooled in an ice bath and sodium cyanoborohydride (30.1 g) is added in small portions over a two-minute period. The resulting suspension is stirred mechanically and over the next 30 minutes enough concentrated hydrochloric acid solution is added dropwise to the reaction mixture to maintain a pH of about 4. The solvent is removed in vacuo to leave a semisolid residue which is dissolved in 300 ml of a 10% solution of hydrochloric acid in a well ventilated fume hood. This solution is diluted with an equal volume of acetone and refluxed for two hours. The volatile components of the mixture are removed in vacuo and the residue is cooled in an ice bath and made basic with concentrated ammonium hydroxide. The white solid which forms is recrystallized from ethyl acetate-heptane to give 52.4 g of the title compound; mp 142°–144° C.

In a process analogous to Example A using appropriate starting materials the following compounds are prepared:

EXAMPLE Aa 4-(3,6-Dihydro-4-phenyl-1(2H)-pyridinyl)]cyclohexanone mp 148°–150° C.

EXAMPLE Ab 4-(4-Phenyl-1-piperazinyl)cyclohexanone mp 137°–140° C.

EXAMPLE Ac

4-[4-(2-pyrimidinyl)-1-piperazinyl]cyclohexanone mp 151°–155° C.

EXAMPLE B

Ethyl 4-oxocyclohexanecarboxylate

Ethyl 4-hydroxybenzoate is reduced to ethyl 4-hydroxycyclohexanecarboxylate according to the procedure described in R. A. Finnegan and P. L. Bachman, *Journal of Organic Chemistry*, Volume 30, pages 4145–4150 (1965). The crude material obtained in this reduction (190 g) is dissolved in 1200 ml of reagent grade acetone. The solution is cooled to 0° C. and 152 ml of a 8 N chromic acid solution (prepared from concentrated sulfuric acid and chromium trioxide) is added dropwise to the mechanically stirred reaction mixture. Enough isopropanol is added to the mixture to discharge its red color and it is then filtered through Celite. The salts are washed with several portions of acetone. The filtrate is evaporated in vacuo. The residue is dissolved in 750 ml of diethyl ether and washed with sodium bicarbonate and brine solutions. After drying, the solvent is evaporated and the residue is distilled to yield the title compound; $bp_{12}$ 125° C.

In a process analogous to Example B using appropriate starting materials the following compound is prepared:

EXAMPLE Ba

Ethyl 4-oxocyclohexaneacetate; bp$_{0.5}$ 100° C.

EXAMPLE C (±)-Ethyl 2-amino-4,5,6,7-tetrahydro-6-benzothiazolecarboxylate

Method A

A solution of ethyl 4-oxocyclohexanecarboxylate (17.5 g) (Example B) in 110 ml of glacial acetic acid and 28.2 ml of a 30% solution of hydrobromic acid in acetic acid is treated with bromine (18.09 g) dropwise. The solution is stirred at room temperature for 30 minutes. The solvent is evaporated in vacuo, and the residue is refluxed with thiourea (8.22 g) in 300 ml of ethanol for 15 hours. The solvent is evaporated and the residue is dissolved in water and made basic with a dilute solution of ammonium hydroxide. A white solid forms which is filtered and recrystallized from ethyl acetate to give 10.24 g of the title compound as a white solid; mp 170°–173° C.

In a process analogous to Example C (Method A) using appropriate starting materials the following compound is prepared:

EXAMPLE Ca (±)-Ethyl 2-amino-4,5,6,7-tetrahydro-6-benzothiazoleacetate; mp 143°–147° C.

Method B

A solution of ethyl 4-oxocyclohexanecarboxylate (5.95 g) (Example B) in 200 ml of anhydrous tetrahydrofuran is added dropwise under nitrogen to a solution of lithium diisopropylamide (prepared from 4.40 g of diisopropylamine and 26.2 ml of 1.6 M n-butyllithium hexane solution) in 200 ml of tetrahydrofuran at −78° C. The mixture is stirred at this temperature for one hour and trimethylsilyl chloride (4.71 g) is added dropwise via syringe. The reaction mixture is allowed to warm to room temperature overnight and the solvent evaporated in vacuo. The residue is triturated with 100 ml of diethyl ether and filtered to remove inorganic salts. Evaporation of the volatile components of the mixture gives ethyl 4-[(trimethylsilyl)oxy]-3-cyclohexene-1-carboxylate as a colorless oil which is reacted with N-bromosuccinimide and thiourea by following the procedure of Example 1 (Method A) to yield the title compound as a white solid; mp 170°–173° C.

EXAMPLE D (±)-Methyl 2-amino-4,5,6,7-tetrahydro-6-benzothiazolecarboxylate

The procedure of M. E. Jung, et al, *Journal of the American Chemical Society*, Volume 103, pages 6177–6185 (1981), is followed to prepare (±)-methyl 4-[(trimethylsilyl)oxy]-3-cyclohexene-1-carboxylate. A solution of 100 g of this compound in 500 ml of dry tetrahydrofuran is cooled in an ice bath under nitrogen and treated sequentially with N-bromosuccinimide (92.91 g) and 20 minutes later with thiourea (39.73 g). The mixture is refluxed under nitrogen for two hours. The solvent is removed in vacuo and the residue is partitioned between chloroform and a dilute solution of ammonium hydroxide. The organic phase is washed with brine and dried over magnesium sulfate. Evaporation of the solvent gives 82.7 g of the title compound; mp 148°–168° C.

EXAMPLE E (±)-2-Amino-4,5,6,7-tetrahydro-6-benzothiazolecarboxylic acid

A solution of (±)-methyl 2-amino-4,5,6,7-tetrahydro-6-benzothiazolecarboxylate (8.5 g) (Example D) in 200 ml of 2N sulfuric acid is refluxed for eight hours. The solution is cooled in ice and adjusted to pH 6 with concentrated sodium hydroxide solution. The title compound precipitates as a beige solid; mp 220°–250° C. (dec).

EXAMPLE F

Ethyl 1,4-dioxaspiro4,5]decane-8-acetate

A solution of triethyl phosphonoacetate (158.7 ml) in 500 ml of tetrahydrofuran is added over a period of two hours to an ice-cold suspension of 60% sodium hydride (38.5 g) in 500 ml of tetrahydrofuran under nitrogen. The reaction mixture is stirred at room temperature for one hour. A solution of 1,4-cyclohexanedione monoethylene ketal (100.0 g) in 500 ml of tetrahydrofuran is added dropwise and the reaction mixture stirred at room temperature for 10 hours. The reaction is concentrated in vacuo and the residue taken up into ethyl acetate and washed with brine. The organic extract is dried (magnesium sulfate) and concentrated to leave 142.7 g of a light yellow liquid consisting of a mixture of isomeric unsaturated esters. A solution of these esters (101.5 g) in 700 ml of ethanol containing 5 g of 5% palladium on charcoal is hydrogenated at 50 pounds per square inch (psi) (H$_2$) for three hours. The mixture is filtered and evaporated in vacuo. The title compound is obtained by distillation; bp$_1$ 110°–115° C.

EXAMPLE G 1,4-Dioxaspiro[4,5]decane-8-acetic acid

A solution of ethyl 1,4-dioxaspiro4,5]decane-8-acetate (50.0 g) (Example F) in 50 ml of 4.8 N sodium hydroxide solution and 400 ml of ethanol is refluxed under nitrogen for two hours. The mixture is concentrated in vacuo to remove the ethanol. The residue is acidified with a saturated sodium biphosphate solution and the mixture extracted with ethyl acetate (2×300 ml). The organic extract is dried over magnesium sulfate, and evaporated in vacuo to give an oily solid which is triturated with hexane and filtered to give 38.25 g of the title compound as a white solid; mp 110°–113° C.

EXAMPLE H

4-Oxocyclohexaneacetic acid

A solution of 1,4-dioxaspiro[4,5]decane-8-acetic acid (36.54 g) (Example G) in 750 ml of a 1:1 mixture of a 10% solution of hydrochloric acid:acetone is refluxed under nitrogen for four hours. The mixture is concentrated in vacuo and the residue extracted with chloroform. The organic extract is dried (magnesium sulfate) and evaporated to leave the title compound as a yellow oil which can be used without further purification.

EXAMPLE I

1-(1,4-Dioxaspiro[4,5]dec-8-ylacetyl)-4-(2-pyridinyl)-piperazine

An ice-cold solution of 1,4-dioxaspiro[4,5]-decane-8-acetic acid (20.0 g) (Example G) and triethylamine (20.9 ml) in 100 ml of dichloromethane is treated dropwise with a solution of isobutyl chloroformate (19.4 ml) in 100 ml of dichloromethane under nitrogen. The resulting solution is stirred at 0° C. for 10 minutes and a solution of 1-(2-pyridyl)-piperazine (32.59 g) in 100 ml of dichloromethane is added dropwise. The mixture is stirred at 0° C. for 15 minutes and then at room temperature for one hour. After washing with 1 L of a saturated solution of sodium bicarbonate, the organic phase is dried over magnesium sulfate and concentrated in vacuo. The crude product is purified by MPLC (silica; ethyl acetate) to give 25.50 g of the title compound as a colorless solid; mp 113°-116° C.

In a process analogous to Example I using appropriate starting materials the following compound is prepared:

EXAMPLE Ia

1-(1,4-Dioxaspiro[4,5]dec-8-ylacetyl)-1,2,3,6-tetrahydro-4-phenylpyridine mp 100°-105° C.

EXAMPLE J

4-[2-[4-(2-Pyridinyl)-1-piperazinyl]ethyl]cyclohexanone

A solution of 1-(1,4-dioxaspiro[4,5]dec-8-yl-acetyl)-4-(2-pyridinyl)piperazine (17.0 g) (Example I) in 500 ml of dry tetrahydrofuran is treated with sodium borohydride (6.81 g) under nitrogen and the resulting suspension is treated dropwise with a solution of boron trifluoride etherate (29.5 ml) in 100 ml of tetrahydrofuran. The reaction mixture is stirred at room temperature overnight. A solution of glacial acetic acid (10.3 ml) in 100 ml of tetrahydrofuran is added dropwise, and the mixture stirred at room temperature for two hours. The solvent is evaporated in vacuo and the residue refluxed with 250 ml of a 10% solution of hydrochloric acid and 250 ml of acetone for two hours. The mixture is concentrated in vacuo to about one-half of the original volume. The remaining aqueous solution is washed twice with ethyl acetate and made basic with ammonium hydroxide. The crude product is extracted into ethyl acetate (2×300 ml). The organic extract is dried over magnesium sulfate and concentrated in vacuo. The reaction mixture is purified by MPLC (silica; 2% methanol, 98% chloroform) to give 9.73 g of the title compound as a colorless solid; mp 104°-106° C.

EXAMPLE K

4-[2-(3,6-Dihydro-4-phenyl-1(2H)-pyridinyl)ethyl]-cyclohexanone

To a stirring suspension of lithium aluminum hydride (9.24 g) in 250 ml of dry tetrahydrofuran under nitrogen is added dropwise a solution of aluminum chloride (10.82 g) in 250 ml of diethyl ether. The mixture is stirred at room temperature for 20 minutes and a solution of 1-(1,4-dioxaspiro-[4,5]-dec-8-ylacetyl)-1,2,3,6-tetrahydro-4-phenylpyridine (27.70 ) (Example Ia) in 500 ml of tetrahydrofuran is added dropwise. The resulting mixture is stirred at room temperature for 12 hours. The reaction is quenched by careful addition of 10 ml of water. After 30 minutes, 44 g of a 25% solution of sodium hydroxide is added dropwise and the mixture stirred for one additional hour. The inorganic salts are filtered through Celite and the filtrate evaporated in vacuo, taken up into 250 ml of a 10% solution of hydrochloric acid and 250 ml of acetone and refluxed for eight hours. The solution is cooled, concentrated in vacuo to remove the acetone, made basic with ammonium hydroxide, and extracted with chloroform (2×250 ml). The organic extracts are pooled, dried over magnesium sulfate, and evaporated to give a semisolid residue which is triturated with 100 ml of diethyl ether and filtered. The title compound is obtained (16.82 g) as a light yellow solid; mp 94°-96° C.

EXAMPLE L

2-Amino-4,5,6,7-tetrahydro-N-[(S)-1-phenylethyl]-(S)-6-benzothiazoleacetamide and 2-Amino-4,5,6,7-tetrahydro-N-[(S)-1-phenylethyl]-(R)-6-benzothiazoleacetamide A solution of 4-oxocyclohexaneacetic acid (28.39 g) (Example H) and triethylamine (30.4 ml) in 800 ml of dichloromethane at −10° C. is treated dropwise with isobutyl chloroformate (26.0 ml). The reaction mixture is stirred at this temperature for 15 minutes and 1(S)-phenylethylamine (26.51 g) is added via syringe. After 30 minutes at −10° C., the mixture is stirred at room temperature for another 30 minutes. The reaction is concentrated in vacuo and the residue partitioned between ethyl acetate (1000 ml) and 1 N hydrochloric acid solution (400 ml). The organic extract is washed with 1 N sodium hydroxide solution and brine, dried (magnesium sulfate), and concentrated in vacuo to leave 67.5 g of crude (S)-4-oxo-N-(1-phenylethyl)cyclohexaneacetamide as a white solid; mp 110°-151° C.

Using the procedure of Example 1 (Method A), (S)-4-oxo-N-(1-phenylethyl)cyclohexaneacetamide is transformed into a mixture of 2-amino-4,5,6,7-tetrahydro-N-[(S)-1-phenylethyl]-(S)-6-benzothiazoleacetamide and 2-amino-4,5,6,7-tetrahydro-N-[(S)-1phenylethyl]-(R)-6-benzothiazoleacetamide. These diastereomeric amides are separated by MPLC (silica; 2% ammonium hydroxide, 98% ethyl acetate). Faster-running compound; mp 137°-139° C.; $[\alpha]_D = -100.2°$ (c=1.04; methanol). Slower-running compound; mp 167°-172° C., $[\alpha]_D = -3.0°$ (c=1.24, methanol).

EXAMPLE M

(+)-1-(2-Amino-4,5,6,7-tetrahydro-6-benzothiazolyl)-acetyl]-4-(2-pyridyl)piperazine A solution of 6.53 g of the slower-running diastereomer (Example L) is refluxed in 300 ml of 3 N sulfuric acid solution (water:dioxane, 1:1) for 72 hours. The dioxane is evaporated in vacuo. The aqueous residue is made basic with ammonium hydroxide and washed with ethyl acetate. The aqueous solution is evaporated to dryness to give a brown solid residue which is triturated with hot methanol:chloroform (1:9) (3×500 ml) and filtered. The filtrate is evaporated to leave 8.3 g of crude (+)-2-amino-4,5,6,7-tetrahydro-6-benzothiazoleacetic acid as a brown oil. A solution of this crude acid in 250 ml of dimethylformamide is treated with 1-(2-pyridy)piperazine (2.76 g) and 1-hydroxybenzotriazole hydrate (2.59 g). The resulting solution is cooled in an ice bath and N,N'-dicyclohexylcarbodiimide (3.49 g) is added. The reaction mixture is stirred at room temperature overnight. The dicyclohexylurea formed is filtered and the filtrate concentrated in vacuo. The residue is partitioned between chloroform and potassium carbonate solution. The organic phase is washed with brine and dried (magnesium sulfate). The crude material is purified by MPLC (silica; 4% methanol, 96% chloroform) to give 5.24 g of (+)-1-[(2-amino-4,5,6,7-tetrahydro-6-benzothiazolyl)acetyl]-4-(2-pyridyl)-piperazine hemihydrate as a foamy yellowish solid; $[\alpha]_D = +44.7°$ (c=1.06; methanol).

In a process analogous to Example M using appropriate starting materials the corresponding compound is prepared as follows:

EXAMPLE Ma (−)-1-[(2-Amino-4,5,6,7-tetrahydro-6-benzothiazolyl)-acetyl]-4-(2-pyridyl)piperazine $[\alpha]_D = -50.3°$ (c=1.0; methanol).

I claim:
1. A compound of Formula I

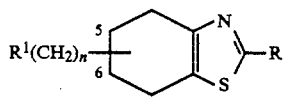

I wherein R is hydrogen, lower alkyl or

wherein $R^2$ is hydrogen, lower alkyl, aryl lower alkyl, lower alkanoyl, aryl lower alkanoyl or aroyl and $R^3$ is hydrogen, lower alkyl or aryl lower alkyl; n is zero or an integer from 1 to 3; $R^1$ is

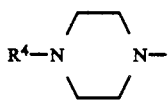

wherein $R^4$ is 2-, 3-, or 4-pyridinyl or 2-, 3-, or 4-pyridinyl substituted by lower alkyl, lower alkoxy or halogen and

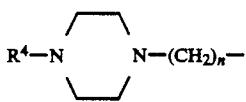

is attached at the 5 or 6 position or the tetrahydrobenzothiazole ring; and corresponding optical isomers thereof; or a pharmaceutically acceptable acid addition salt thereof.

2. A compound according to claim 1, in which R is hydrogen or

wherein $R^2$ is hydrogen, lower alkyl, lower alkanoyl or aroyl and $R^3$ is hydrogen, or lower alkyl and $R^1$ is

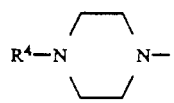

wherein $R^4$ is 2-pyridinyl.

3. A compound according to claim 2, in which R is hydrogen or

wherein $R^2$ is hydrogen, lower alkanoyl, or aroyl and $R^3$ is hydrogen and $R^1$ is

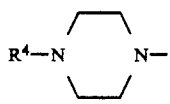

wherein $R^4$ is 2-pyridinyl.

4. A compound according to claim 3 selected from the group consisting of
(±)-4,5,6,7-Tetrahydro-6-[4-(2-pyridinyl)-1-piperazinyl]-2-benzothiazolamine;
(±)-4,5,6,7-Tetrahydro-6-[[4-(2-pyridinyl)-1-piperazinyl]-methyl]-2-benzothiazolamine;
(±)-4,5,6,7-Tetrahydro-6-[[4-(2-pyridinyl)-1-piperazinyl]-methyl]benzothiazolamine;
(±)-4,5,6,7-Tetrahydro-6-[2-[4-(2-pyridinyl)-1-piperazinyl]ethyl]-2-benzothiazolamine;
(±)-4,5,6,7-Tetrahydro-5-[4-(2-pyridinyl)-1-piperazinyl]-2-benzothiazolamine;
(±)-4,5,6,7-Tetrahydro-5-[[4-(2-pyridinyl)-1-piperazinyl]-methyl]-2-benzothiazolamine;
(±)-4,5,6,7-Tetrahydro-5-[2-(4-(2-pyridinyl)-1-piperazinyl]ethyl]-2-benzothiazolamine;
(±)-N-[4,5,6,7-Tetrahydro-6-[4-(2-pyridinyl)-1-piperazinyl]-2-benzothiazolyl]benzamide;
(±)-N-[4,5,6,7-Tetrahydro-6-[4-(2-pyridinyl)-1-piperazinyl]-2-benzothiazolyl]acetamide;
(±)-N-[4,5,6,7-Tetrahydro-6-[4-(2-pyridinyl-1-piperazinyl]-2-benzothiazolyl]-2-methylpropanamide;
(+)-4,5,6,7-Tetrahydro-6-[4-(2-pyridinyl)-1-piperazinyl]-2-benzothiazolamine;
(−)-4,5,6,7-Tetrahydro-6-[4-(2-pyridinyl)-1-piperazinyl]-2-benzothiazolamine;
(+)-4,5,6,7-Tetrahydro-6-[2-[4-(2-pyridinyl)-1-piperazinyl]ethyl]-2-benzothiazolamine; and
(−)-4,5,6,7-Tetrahydro-6-[2-[4-(2-pyridinyl)-1-piperazinyl]ethyl]-2-benzothiazolamine.

5. A method of treating schizophrenia comprising administering to a host suffering therefrom a therapeutic effective amount of a compound according to claim 1 in unit dosage form.

6. A pharmaceutical composition adapted for administration as a dopaminergic, antipsychotic orantihypertensive agent comprising a therapeutic effective amount of a compound according to claim 1 in admixture with a pharmaceutically acceptable excipient, diluent or carrier.

* * * * *